United States Patent
Blair et al.

[11] Patent Number: 6,026,818
[45] Date of Patent: Feb. 22, 2000

[54] TAG AND DETECTION DEVICE

[75] Inventors: William Blair, Worcester, Mass.; Jeff Port, New York, N.Y.

[73] Assignee: Blair Port Ltd., New York, N.Y.

[21] Appl. No.: 09/033,340

[22] Filed: Mar. 2, 1998

[51] Int. Cl.[7] .................................................. A61B 19/00
[52] U.S. Cl. ............................................................. 128/899
[58] Field of Search ................................. 128/897–899; 604/362; 324/260

[56] References Cited

U.S. PATENT DOCUMENTS

| | | | |
|---|---|---|---|
| 4,193,405 | 3/1980 | Abels | 604/362 |
| 5,107,862 | 4/1992 | Fabian et al. | 128/899 |
| 5,188,126 | 2/1993 | Fabian et al. | 128/899 |
| 5,329,944 | 7/1994 | Fabian et al. | 128/899 |
| 5,664,582 | 9/1997 | Szymaitis | 128/898 |

*Primary Examiner*—Samuel Gilbert
*Attorney, Agent, or Firm*—Graham & James LLP

[57] ABSTRACT

A method and device for the detection of unwanted objects in surgical sites, including a medically inert detection tag which is affixed to objects such as medical sponges or other items used in body cavities during surgery. The detection tag is of minimal size with a length of about 8 mm in the shape of a bead (ovate or circular) of a medically inert hard material such as plastic or glass, with a single signal emitter such as a miniature ferrite rod and coil and capacitor element imbedded therein. Alternatively, the tag includes a flexible thread composed of a single loop wire and capacitor element, within a protective flexible elongate casing which is sewn or woven into the fabric of the sponge. A detection device is utilized to locate the tag by pulsed emission of a wide band transmission signal. The tag resonates with a radiated signal, in response to the wide band transmission, at its own single non-predetermined frequency, within the wide band range. With the pulsed emissions, the return signals build up in intensity at a single (though not predefined) detectable frequency over ambient noise whereby utilizable small, economical tags readily provide recognizable detection signals.

18 Claims, 5 Drawing Sheets

TAG AND DETECTION DEVICE

FIELD OF THE INVENTION

This invention relates to detection of tagged objects and devices and particularly objects and devices utilized in body cavities during surgery and most particularly to surgical sponges which are frequently "lost" in such body cavities.

BACKGROUND OF THE INVENTION

During a surgical procedure, and especially in procedures where the chest or abdomen is open, foreign objects such as surgical sponges, needles and instruments are sometimes misplaced within the patient's body cavity. In general any foreign object left within the body can cause complications, (i.e. infection, pain, mental stress), excepting objects such as clips and sutures that are purposely left as part of a surgical procedure.

Presently there are two surgically acceptable procedures for detection and removal of the foreign objects. Firstly, a count of all objects used in the operation is kept by surgical support staff. Secondly, x-ray detection is used to locate foreign objects.

It is not uncommon however, for object counts to be incorrect, because of human error, and the general chaos attendant with a surgical procedure. Furthermore, even x-ray detection is not flawless. Despite the fact that objects such as surgical sponges, (one of the most frequent objects left in the body), are embedded with an x-ray opaque material to make them more readily detectable, surgical sponges are often crushed into very small areas within a flesh cavity, whereby x-rays are not always able to sufficiently highlight them for detection. Furthermore, and most detrimentally, an x-ray is a time delayed detection method because of the requirement for film development (even with quick developing films). A patient will often be completely sutured closed before x-ray results are obtained, which may indicate the location of a foreign object within the patient. The detection delay, may therefore result in the necessity for the surgical team to re-open the patient, thereby increasing the morbidity of the operation.

The prior art is replete with means for the detection of foreign objects (aside from x-ray analysis) which may remain in body cavities following surgery. However, such means have either been prohibitively costly, involve detection devices which are too large to be meaningfully useful (i.e., they often impede utilization of the objects they are intended to locate) or simply do not provide effective detection.

There have been a number of devices described in numerous patents for detection of surgical objects such as surgical sponges, which operate by means of marker or tag systems using electromagnetic, magnetomechanical, electromechanical detection techniques. For example, U.S. Pat. No. 2,740,405, issued to Riordian, describes the use of a radioactive tracer for detection of the foreign objects. This method is however, among other things, subject to problems involving the hazards of storage and disposal of radioactive materials.

In another example of detection devices and methods, U.S. Pat. No. 3,422,816, issued to Robinson et al., teaches a technique wherein sponges are marked with a flexible plastic impregnated with paramagnetic or ferromagnetic powders which are detected by a metal detector. However, this method is limited by the small signals obtainable (making detection unreliable), and the lack of discrimination from other magnetically susceptible metal objects, such as surgical staples, which are intended to remain in the body.

In an improvement over the preceding patent, in U.S. Pat. No. 3,587,583, issued to Greenberg, sponges were marked with magnetized particles whose presence is detectable with magnetodiodes. Nevertheless, such method has also not proven to be practical or reliable.

A spate of patents disclose electronically based signal devices, such as disclosed in U.S. Pat. No. 4,114,601, issued to Ables, which discloses use of a gyromagnetic transponder for marking a sponge. Detection is accomplished by a mixing of two frequencies beating the tag. The method however appears impractical because of transmission loss at its operating frequency of 5 Ghz.

In theory, electronic locators should be ideal for the detection of surgical sponges. However, as a practical matter, it is difficult to make a small tag element with sufficient signal strength for reliable detection and at an economic cost. More importantly, the increased size of a tag element often results in a detrimental effect on the utilization of the object it is intended to locate. Thus, surgical sponges, the most common item for which detection is most important, are useful only if they can be deformed for use. However, deformation often distorts large tag elements and small tag elements do not provide sufficient signal strength for detection. A non-deformable large tag is totally counter-productive since it would effectively eliminate the usefulness of a sponge which must be deformed for use.

As an example of miniature electronic tags, U.S. Pat. No. 4,658,818, issued to Miller et al, discloses the use of a miniature electrical oscillator which is attached to each surgical implement and actuated at the time of surgery. Detection occurs by coupling the oscillation with the patient's tissue. However, because of interference considerations, this method does not appear to be practical.

In relatively recent U.S. Pat. No. 5,456,718, issued to Szymaitis, a marker is made of non-magnetostrictive or soft magnetic material which will emit known selected harmonic frequencies when exposed to alternating electromagnetic field. However, in practice, this creates a large non-deformable region within the sponge thereby interfering with its function.

In U.S. Pat. No. 5,105,829, issued to Fabian et al, a battery powered marker is disclosed which uses capacitive coupling of radio signal to tissue. However, for signal couple reasons the method is impractical.

In U.S. Pat. No. 5,190,059, Fabian et al teach a battery powered tag used in conjunction with a zone marker housing or field generator. Detection is effected as a result of characterizable field disturbance by the tag. The invention appears impractical since many surgeries would be obstructed by the addition of a zone housing.

In U.S. Pat. No. 5,057,095, Fabian et al teach marking surgical instruments with three types of resonant markers which produce identifying characteristics when exposed to an alternating magnetic field. First, there is a mangnetome-chanical marker. Second, there is a magnetostrictive marker. (Both these devices are however susceptible to pressure and stress making them impractical in an environment, e.g., sponge, requiring compression, with pressure and stress as a function thereof.) Third, there is an electromagnetic LCR circuit. The markers described in the Fabian art are similar to security tags used in commercial retail anti-theft. As such they are susceptible to failure as they are deformed.

Surgical objects such as sponges must be deformable to conform to body cavity work area. If the tags are shrunk and encapsulated so that they would take up a sufficiently small deformation resistant area within a sponge, they could be used without impeding the function of the sponge. However, as the area of the described tags is shrunk, their coupling will decrease, making them almost invisible to a typical anti-theft system (to which the Fabian system is akin) and thus any detection system contemplated for their use in surgery.

Another very important characteristic absent from many of the prior art expedients is, besides being effective in use, the economics involved. Thus, many of the tags described in the prior art cost well in excess of two dollars per tag. While this is usually dwarfed by actual surgical costs, it is nevertheless a sufficiently significant amount to cause concern among potential users.

SUMMARY OF THE INVENTION

It is therefore an object of the present invention to provide a method and combination device suitable for detection of the presence of objects and particularly suitable for use in detection of objects such as surgical sponges which may have been left behind during surgery, wherein the device comprises detection tags which are sufficiently small, whereby they do not impede use of an object such a surgical sponge, or are larger but flexible, and are reliable in discriminating detection, and yet are economical for widespread use in objects such as garments.

It is a further object of the present invention to provide a detection system in which the tags are sufficiently small whereby, though they are not deformable, they do not impede sponge utilization but which nevertheless provide a large, reliably detectable signal.

It is yet another object of the present invention to provide such tags as being integrated into the fibers of the sponge and wherein the cost thereof is very minimal.

Generally the present invention comprises a method, and economical device utilizing the method, for the electronic detection of objects and particularly foreign objects not intended to remain in a human body cavity during or after surgery wherein detection tags do not affect flexibility of surgical sponges but which provide reliable and strong detection signals. In accordance with the present invention, the method comprises the steps of:

a) attachably providing objects such as may be used in surgery, such as surgical sponges, with tag means which respond to an emitted wideband signal, with a single non-predetermined frequency return or response signal;

b) after surgery or as required, scanning the site of the object with interrogation scanning means which emit a pulsed wideband signal which includes the frequency at which the tag means (and objects attached thereto which may have been inadvertently left within a surgical site), respond with a single narrow return or response signal for each pulse; with said pulsed wideband signal being of sufficient duration to cause the return signals from the tags, in response to each of the wideband interrogation pulses, to become sufficiently strong for reliable detection by detection means as a narrow peak signal distinguishable from background noise, for detection of the tag and object attached thereto for removal. The exact frequency of the peak signal both before and after detection is however immaterial since it is only a peak which is detected and not the position of the peak.

The above objects, features and advantages of the present invention will become more evident from the following discussion and drawings in which:

DETAILED DESCRIPTION OF THE INVENTION

Figure 1:
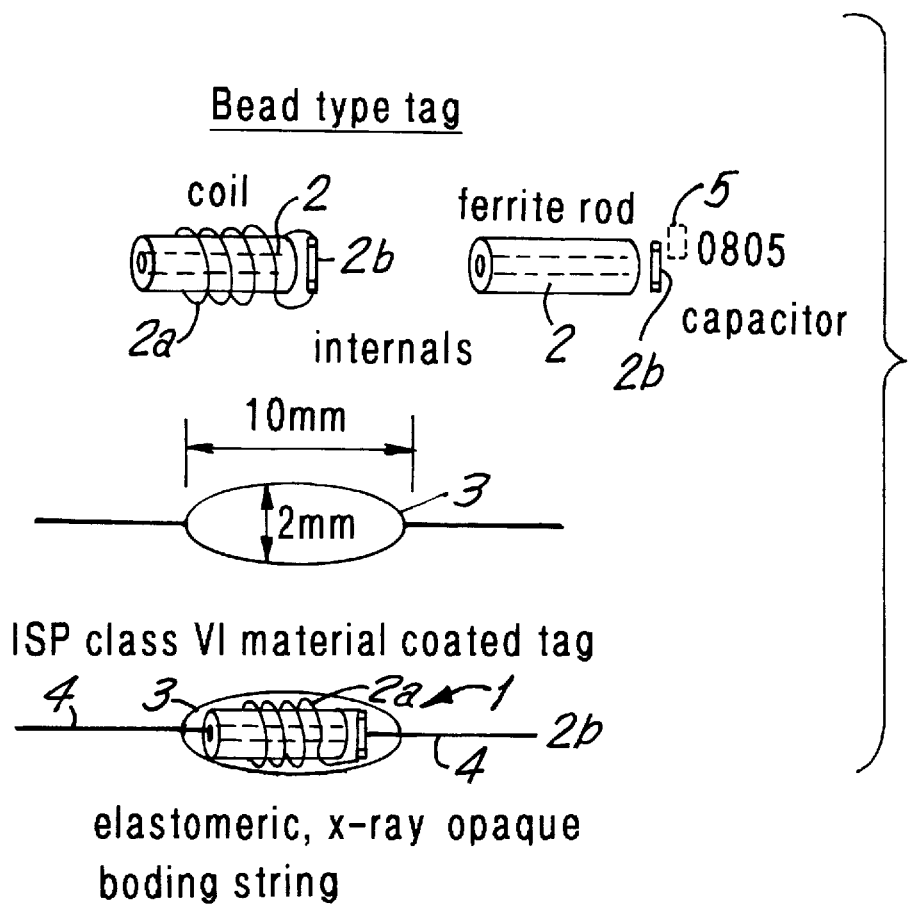
FIG. 1 is an exploded view of a bead type tag used in the present invention.

The device used in the aforementioned detection method, comprises an electronic signal emitting detection device preferably in the configuration of a movable wand with an interrogation ring (i.e., emitting antenna), and one or more tag elements (for each object to be detected) with each tag being of a size which is sufficiently small as not to impede function of deformable objects such as surgical sponges, and preferably no greater than about 12 mm in its largest dimension. The tag element is preferably either electrically insulatively encapsulated in a bio-inert (if used in a surgical environment) hard plastic or glass, and is configured in the form of a bead or is contained within a electrically insulative bio-inert flexible thread element (preferably elastic) which is attached to the object to be detected (in such embodiment the flexible, i.e., deformable, thread can even be in the area of about 3" in length). If the object is a surgical sponge, the bead may be directly heat sealed to the threads of the sponge or adhered with a medically acceptable adhesive or may be provided with an attaching thread for attachment thereto. Tags already in a thread configuration are directly woven into the sponge material where conditions of size are less stringent.

The tag element contains components which provide a return signal in response to the signal emitted from the detection device. The tags are very simple in nature (i.e., inexpensive, yet effective, but only when used in accordance with the present invention) and generally comprise a single signal emitting element such as an encapsulated miniature ferrite rod with wire winding, coupled with a capacitive means such as a capacitor for use in a bead embodiment, or a simple single loop wire, with winding, contained within an elastomeric coating as a thread element. An optional diode may be utilized to protect against tag-burn-out where an electric arc-weld type device known as a bovie, with applied electrical current, is contemplated for use as a scalpel (alternatively the number of wire windings may be reduced to reduce any burn-out effect) proximate thereto. The tag is inexpensive with a current cost on the order of about five cents (six cents with a diode).

The tag emits a small response signal, of general but not specifically known frequency, which would normally not be readily detectable because of its weak strength and non-predetermined nature. However, in accordance with the present invention, the signal emitting detection device comprises pulsed signal emitting means which cover a signal range which includes that of the tag. The pulsed signals trigger a continuing response signal from the tag, in its single frequency, which increases in a very narrow band to a point where it becomes differentiated from background noise and it is detected within the wideband range by the signal detector, as an indication of the presence of the tag. Since the precise frequency of the signal response is not necessary or even pre-determined, expenses in electronics for emission and detection are also minimized. Because of the immediate turn off of the signal during pulses the tag return signal is very quickly located (on the order of microseconds instead of milli-seconds, from transmitter turn-off) and even a low Q tag is utilizable as opposed to the high Q tags required in the prior art.

Tag characteristics, in addition to those mentioned above, and especially with respect to medical applications, include ruggedness, whereby the tag should be able to withstand high temperatures, and pressure from surgical instruments, (i.e. clamps) as well as all liquid immersions, bovie emissions, and high voltage cardiac defibrillation. The tags should be crush proof and the bead tags should be non-deformable under surgical use. Bio-inert plastics, such as are used with prosthetics, as well as bio-inert glass are useful for the encapsulation protection of the radiating elements.

It is preferred that the tags be detectable from a distance of at least about 12 to 18 inches from a handheld mobile detector. In addition, all orientations of the tag should be accommodated within the aforementioned range.

In a preferred embodiment, the detector device is adapted to be hand-held and thus lightweight, and wand-like in configuration. This obviates the need for special bed installation or room adaptations, with detection equipment, as utilized in some prior art embodiments. The detector of the present invention is accordingly portable and movable with the patient.

In a preferred embodiment, the detector device is provided with a radar-like system coupled with passive magnetic technology. The system for detecting surgical sponges is defined by two basic elements:

a) a detection wand—the hand held unit which the surgeon or surgical staff member can use within approximately 12 to 18 inches of proximity to the patient and the surgical site, for verification of object removal; with the head of the device, being preferably a loop wire antenna, which can be sterilized and replaceable, for open wound intrusion; with the wand containing transmission and receiving signal means; and b) a tag which is excited by a signal from the detection wand, with detectable ring-back response.

In a preferred embodiment of the present invention, the detection system uses a ring back technique (which excites a tag element, previously placed on a medical instrument or on/in a surgical sponge), by radiating magnetically coupled energy to the tag, through the loop antenna. The use of magnetic coupling is particularly preferred since magnetic coupling is almost inert to tissue and water immersion, conditions most prevalent in a surgical environment.

In operation, the transmit cycle from the detection wand utilizes a pulsed method to excite the tag(s) with signals over a fairly wide bandwidth wherein sinusoidal components of the resonant tags exist in the pulses. This permits the use of economical tag components since center frequency is not required to close tolerances. Furthermore, the pulsed transmissions allow the system to pump more energy into the tag through several pulses, before ring back occurs, with extending ring back duration, thereby effectively increasing the range of detection to usable levels. The tag, when excited, transmits an image signal of its resonance decay, via magnetic coupling, back to the detection wand which contains a receiver circuit.

The preferred detection wand has a single loop antenna structure shared for both transmit and receive functions, with one loop for transmit and receive, through which the image of the numerous tag return signals (in response to the pulse signals) are processed, to create better signal to noise performance. The signal transmitter therein is preferably multi turn single loop, wherein band of operation frequency lowers for operational inductance of wire or by shrinking the diameter of the loop. Return signal averaging is used to "see" the signals (as a single enhanced signal) through noise. This "visibility" condition is a result of the multiple signals being added to each other directly whereas noise tends to add at its square root, thereby resulting in an enhanced single narrow band signal rising from the background noise levels. In the preferred embodiment a custom box-car integrator is used for this purpose.

Signal processing technique allows the system to characterize a tag via its ring back response and signals which are not tags are easily discarded by comparison to the characterized signature map. This provides detection results which are far superior to traditional ring back systems which rely on either resonance or center frequency detection based on phase shift around center frequency. Reliance on resonance characterization requires either a very tight tolerance of tag components, and or a sweep transmitter function. In contrast, The present system can be wideband for transmission, but extremely discriminating between tags and other objects, without added complexity.

In electronic detail of a preferred embodiment, the pulse generator is set to emit pulses to excite a range of frequency components. The pulses are controlled for duration and interval to maximize energy transfer to the tag over a desired bandwidth. The pulses are sent through a driver and amplified to an appropriate signal level and a transmit amplifier is designed to shut off quickly. To accomplish this, an untuned transmitter is utilized, which relies on the pulse method to insure energy transfer to the resonant tag.

It is noted that tuned transmitters have been used in the prior art to excite resonant tags because the energy transfer efficiency to the tag is high. However, in accordance with the present invention, an untuned transmitter is used because of its useful shut off time with respect to pulsed signals. The use of pulses, as described, makes up for the poor energy transfer since multiple pulses build additive energy into the tag.

In accordance with the present invention, the receiver is also wideband whereby it can see tags over a wide spectrum benefitting from fast transmitter signal decay. The receiver further comprises limiters to insure that the transmit cycle does not saturate it. Once a signal is amplified by the receiver it is sampled by a sample-and-hold circuit/analog to digital Converter, or, in a preferred embodiment, a digitally controlled phase sensitive averager.

Use of an analog to digital converter is however only useful if an optimal DSP technique is to be applied. The time when a signal is sampled is controlled from a TX inhibit clock and control logic in order to insure that a signal captured is at the appropriate time from the transmitter shut off time. Signal processing such as averaging is applied either in through clocking with the sample and hold or summing circuit or by the microprocessor or a DSP. In effect, the averaging technique is similar to a synchronous detector creating a super narrow digital like band pass function (increasing signal to noise of tag return signal).

If a microprocessor is used, it can then store the output of an analog to digital converter. In addition, the microprocessor can be used to characterize ring signature. Depending on the level of complexity of signal processing which may be necessary, the DSP may not be needed or could be external.

In normal operation the transmitter, while it is exciting the tag, is blocking any possible return signal from the tag. That is the system is, in effect, half duplex. Accordingly, one of the major problems encountered in design of a detection wand is reducing the turn off time of the transmitter signal. When the transmitter is on, the tag will be excited and will also radiate a return signal. At the time the transmitter is turned off the tag is at its peak amplitude of radiated signal. But the transient transmitter signal is still present, so the tag signal will not be easily visible until some time later. The transient from the transmitter is from capacitive and inductive components in the transmitter/receiver circuitry and exists even if the transmitter is shunted at turn off. Accordingly, the transmitter/receiver circuit of the present invention is made wideband using low loop capacitance in the analog front end. Thus, greatly improved distance or sensitivity are achievable with small low cost tags having weak signal return.

The present invention is unique by, in effect, using the same excitation frequency component to power the tag and to receive ring back from the tag while being wide band in design. And it is in fact the combination of wideband design coupled with signal processing technique that allows performance of range, tag cost and tag size.

Since surgical procedures involve traumatic procedures, an important aspect of the present invention is that the tags remain attached to the sponge or instrument to be located. Accordingly, the present invention encompasses means for the detachable resistant attachment of the tag to the sponge or instrument. Because of the more severe use (i.e., deformation, involved in sponge use, good attachment thereto is most problematic).

The tags of the present invention, in one embodiment are made into a hard object to resist deformation, and coated with an insulative, bio-friendly and inert shell and is preferably a ferrite core with some loop wire and a capacitor (optionally with a diode for burn-out protection) contained within a 5 mm–12 mm oval shape. A string is integrated into the encapsulating shell to accommodate the tag to be integrated in the cloth manufacturing procedure used in manufacturing the sponge.

In another embodiment a rivet button cell is attached to a corner of the sponge material. For a lap pad the button cell may be added to the lap pad drape loop extension. Alternatively the tags can be adhered to the substrate to be detected by materials such as surgical adhesive implantable FDA USP class VI.

As described above, the detector and tag provide positive signal evidence (audio or visual, e.g., at sufficient signal strength, an LED signal lights up) that a sponge or similar object remains in a body cavity (or that an object is located within a scannable area). However, because of electronics and cost considerations, exact location is not as desirable and is often not as necessary, since mere knowledge of the presence of a sponge is sufficient for a surgical team to quickly manually locate the object within a body cavity (i.e., in the location where sponges were actually used). It may however, be desirable to actually locate the object or at least narrow the range of the site in which the object may be located. Accordingly, detectors of different ranges may be utilized, once the presence of an object has been determined. These detectors may be modified in antenna (or loop) dimension or in power used for signal emissions. With the latter, a single detector can be used, with variable power output, in stages, with successive narrowed ranges to locate the "lost" object with greater precision.

A fixed repetition rate of putting out pulse sequences to excite tage could be susceptible to continuous wave noise (i.e., signals close to the tag frequency). Accordingly, in a further preferred embodiment, the pulse signal frequency is move around in random fashion to make it very difficult for continuous wave noise to affect the system, since it will become very out of phase with the tag resonance. This is similar to a spread spectrum approach in frequency hopping.

In a further embodiment, broad band noise such as is generated with lightning or use of a bovie, is not treated as an adding sample of pulse signal return by tag and is excluded by sampling and sinking to ground.

To ensure that no null field couplings are encountered by the detector wand, such as may result from orientation of the tags, the tags may be initially configured with three orthogonal tank windings. These comprise horizontal and vertical tank circuits in addition to the center tank circuits described for use with the tags. With these additional tank circuits, there is always a loop coil on the tag which will have field lines from the detector wand cutting or passing therethrough. This avoids any misreadings caused by simple placement of the detector wand on the site, instead of with a lateral waving motion.

It is understood that with the three orthogonal tank windings, the geometry of the tag may be varied, such as to enhance its reproducibility, and various tag shapes include cubic, cylindrical, spherical, etc.

DETAILED DESCRIPTION OF THE DRAWINGS AND THE PREFERRED EMBODIMENTS

With specific reference to the drawings, in FIG. 1, a tag 1 in the form of an oval bead, with dimensions of about 8 mm length and 2 mm diameter, is shown with encapsulated miniature ferrite rod 2 with coil 2*a* and capacitor 2*b*. Hard bio-inert plastic 3 encapsulates the coil, rod and capacitor to protect it from damage from pressure and body fluids. Elastomeric, x-ray opaque bonding strings 4, serve as a means by which the bead is attached to a surgical sponge. Because of its very small dimensions it does not impede deformation of the sponge to which it is attached. Diode 5, shown in dotted line outline, is optionally included as electrical protection against electrical burnout from proximate electronic instruments.

Figure 2:
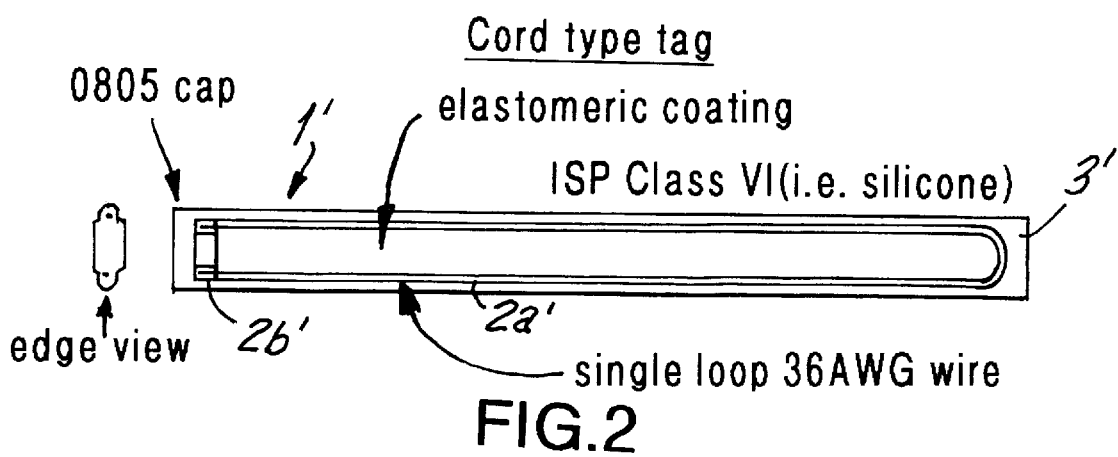
FIG. 2 is a cross section view of a thread type tag used in a second embodiment of the present invention.

In FIG. 2, a second tag embodiment 1' is shown in the form of a thread with single loop wire 2*a*' with capacitor 2*b*' enclosed within an elastomeric coating or sleeve 3'. The diameter of such tag is similar to that of the bead embodiment of about 2 mm but because of its high flexibility, its length can up about 3" (about 75 mm) and it provides its own thread-like attachment means.

Figure 3:
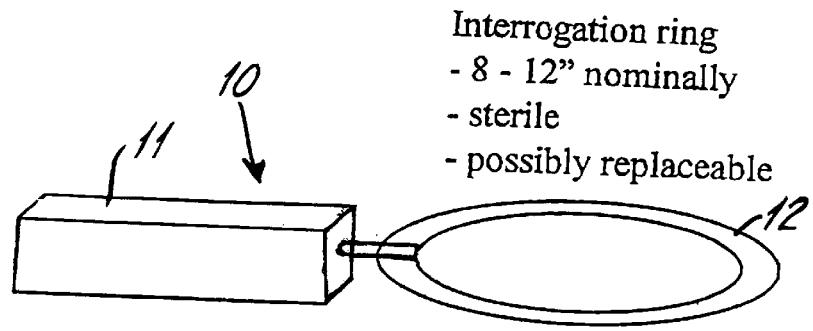
FIG. 3 depicts a typical configuration for the hand held detector of the present invention.
Figure 6:
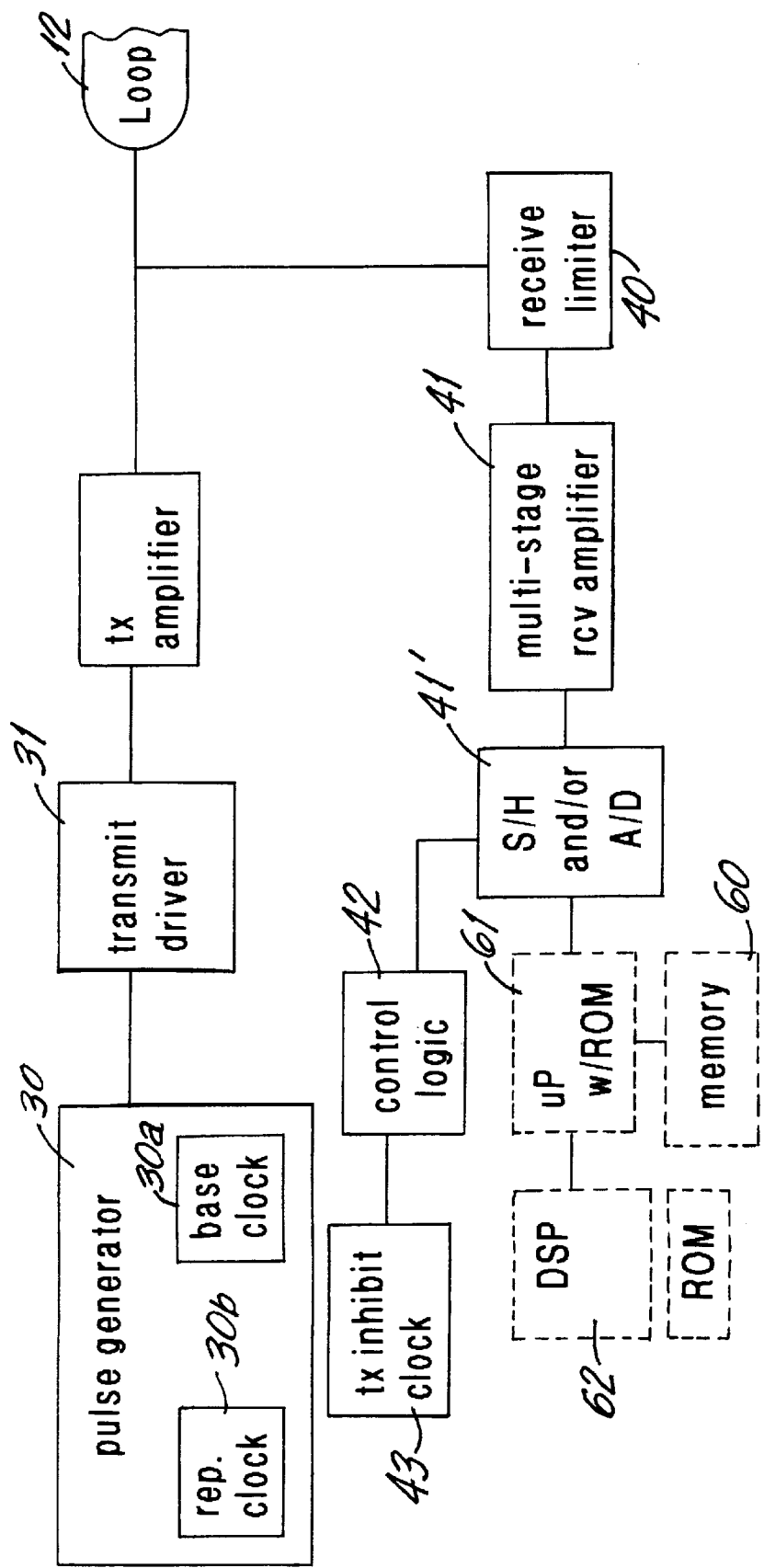
FIG. 6 is a block diagram of the electronics utilized in the detector of FIG. 3.

The bead 1 of FIG. 1 and the thread 1' of FIG. 2 are detected by interrogation/detection device 10, shown in FIG. 3, which comprises handle 11 (with contained electronics, as schematically set forth in the block diagram of FIG. 6, with power supply source of battery or transformer and standard AC electrical connection). Interrogation and receiving ring 12 is an antenna ring with a nominal diameter of between 8–12". Since the ring 12 is in proximity to the surgical site for detection, it is sterile and removable for sterilization or replacement. As shown in dotted line it may be replaced with a smaller diameter ring for more precise location once it has been determined that a "lost" object is present.

Figure 4:
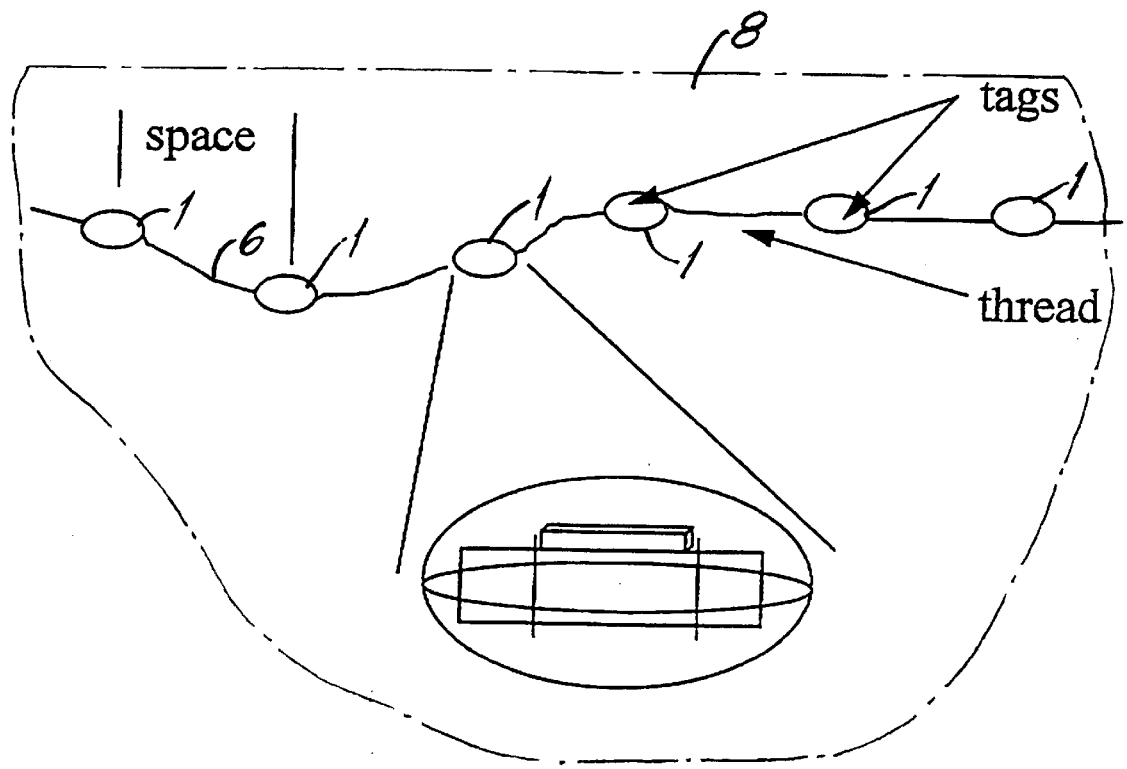
FIG. 4 depicts a thread for weaving into a surgical sponge having multiple beads of the type shown in FIG. 1.

As shown in FIG. 4, a thread 6 with multiple beads 1 is bonded, stitched or woven into the fabric of surgical sponge 8, as a low cost detection tag with increased signal strength.

Figure 5:
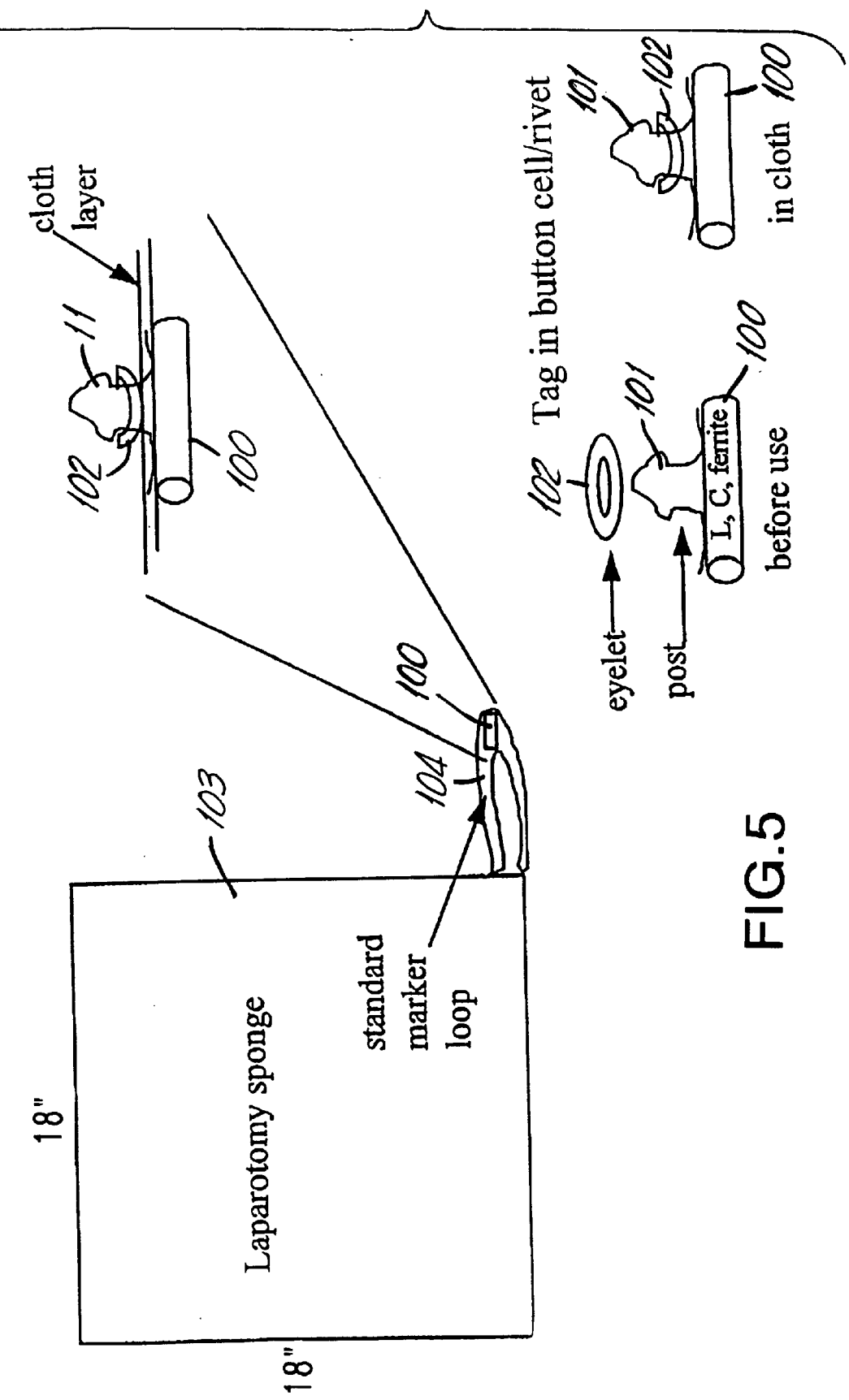
FIG. 5 depicts a manner in which the tag bead of FIG. 1 is attached to a laparotomy sponge with a rivet attachment.

In another embodiment, as shown in FIG. 5, tag 100 is provided with a rivet attachment member 101 and eyelet 102 whereby the tag is attached to a laparotomy sponge 103 which is typically provided with standard marker loops 104.

Figure 7:
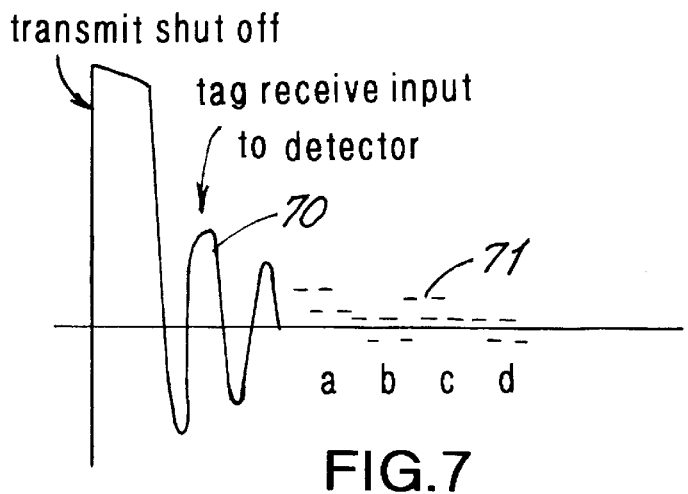
FIG. 7 is a graphical depiction of the wideband signal and the narrow return signal of the tag as differentiated from background noise.

In the embodiment shown, the electronics for both interrogation and reception of return signal are contained within the device shown in FIG. 3. As further shown in FIG. 6, for the interrogation the device contains a pulse generator 30 with base clock and rep. clock 30a and 30b, as well as transmitting driver 31 and tx amplifier as the signal goes to antenna loop or ring 12. For receipt and analysis of a return signal the loop ring 12 receives the signals from any tags which may be present within the interrogation range thereof (of up to about 18" and generally within the range of 12–18"), with the signal passing receive limiter 40, multi-stage receiving amplifier 41, SH and/or A/D 41, to control logic 42 and tx inhibit clock 43. Random access memory 60, uP with ROM element 61 and DSP with ROM 62, shown in dotted lines, control and analyze the pulse signal and return signals. The return signal 70 shown in FIG. 7, rises from background noise 71 for detection by either or both audio or visual alarm which intensifies as the detector nears the tag, for the location of the sponge (or other object attached thereto).

Figure 8:
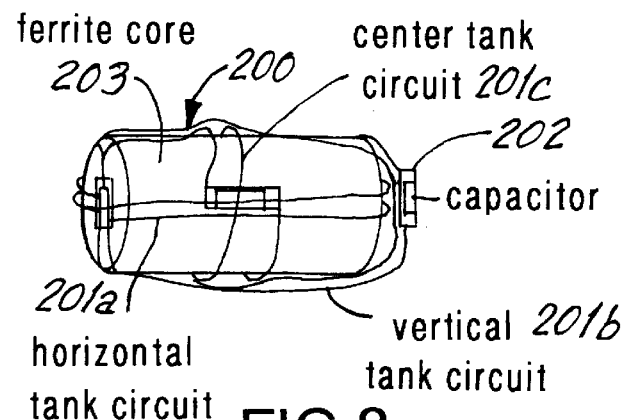
FIG. 8 is a side view of another tag embodiment having three orthogonal tank windings to ensure detector wand cutting of a field line regardless of tag orientation and manner of wand deployment.
Figure 9A:
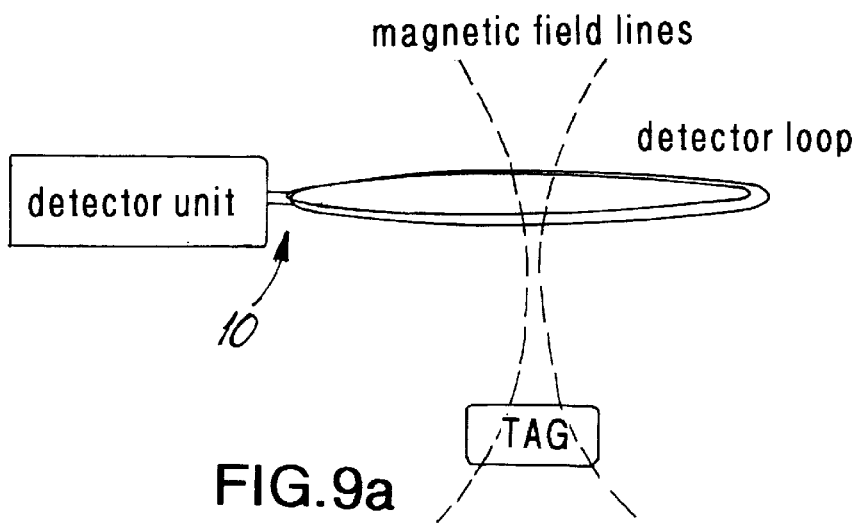
FIGS. 9a and 9b depict detector wand deployment relative to a tag and various possible tag orientations with respect to marked field lines.
Figure 9B:
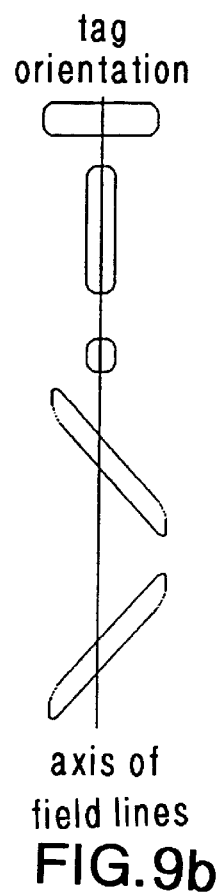

As shown in FIG. 8, a tag 200 which is detectable regardless of orientation is provided with three orthogonal tank circuits 201a, 201b and 201c, respectively shown as horizontal and vertical in addition to the center tank circuit previously described. A single capacitance element 202 is utilized in addition to the ferrite core 203. As shown in FIGS. 9a and 9b, deployment of detection wand 10 detects magnetic field lines regardless of tag orientation.

It is understood that the above description and drawings are only illustrative of the present invention and that changes may be made to the electronics as well as the configuration and components and composition of the tags and detector device as well as the nature and place of the location detection and the relative arrangement thereof, without departing from the scope of the present invention as defined in the following claims.

What is claimed is:

1. A device for the electronic detection of an object within a defined area, said device comprising at least one minimally sized, low Q detection tag element for affixation to said object, without impeding operative use of the object, wherein said tag element comprises a single electronic signal emitter contained within protective means for electrically insulating said tag element; said device further comprising an electronically operable interrogation and detection member adapted to locate the tag element within a predetermined distance therefrom, wherein the interrogation and detection member comprises means for the emission of pulsed wide band transmission signals which includes, within the wide band, a signal which activates the single signal emitter to provide a response signal, and means for the reception and analysis of said response signal; wherein multiple pulsed signals cause increasing intensity of the return signals of the minimally sized tag element to build up in intensity at a single detectable frequency over ambient electronic noise levels to permit detection of the tag element and the object to which the tag element is attached.

2. The device of claim 1, wherein the tag element comprises a bead configuration with a length of up to 12 mm and wherein the tag comprises a single response signal emitter encapsulated within an electrically insulative bio-inert hard plastic.

3. The device of claim 2, wherein the single response signal emitter comprises a ferrite rod and a coil wire therearound with means for providing a capacitance.

4. The device of claim 3, wherein the single response signal emitter further comprises a protective diode adapted to prevent accidental burn-out thereof resulting from electrical equipment being brought into proximity therewith.

5. The device of claim 3, wherein the tags are configured with three orthogonal tank windings, comprising horizontal and vertical tank and center tank circuits.

6. The device of claim 2, wherein said bead configuration comprises means for attachment to the object.

7. The device of claim 6, wherein a defined area is a surgical site, said object is a surgical sponge and said means for attachment comprises flexible threads anchored in the bead and adapted for attachment to the threads of the sponge.

8. The device of claim 6, wherein said object is a laparotomy sponge and said means for attachment comprises a rivet attachment member and an eyelet member whereby the tag is attached to a marker loop of the laparotomy sponge.

9. The device of claim 1, wherein the single response signal emitter comprises an electrically insulative flexible thread element comprising a single loop wire with multiple turns with means for providing a capacitance, within a flexible casing.

10. The device of claim 1, wherein the interrogation and detection member comprises a single removable loop antenna attached to a handle, said handle having contained therein electronic means for said pulsed wideband transmission and electronic means for detecting and analyzing said response signals.

11. The device of claim 10, wherein said interrogation means comprises an untuned transmitter.

12. A method for the electronic detection of a foreign object used during surgery but not intended to remain in a human body cavity after surgery; said method comprises the steps of:

a) attachably providing the foreign object used in surgery, with at least one low Q tag element which does not interfere with utilization of the foreign object, wherein said tag element contains means which respond to an emitted wideband signal, with a single, non-predetermined, response signal;

b) after surgery, scanning a surgical site with interrogation means for scanning wherein said means for scanning emits a pulsed signal which includes a frequency at which the tag element responds with a single response signal for each pulse; with said pulsed signal being of sufficient duration to cause the return signals from the tag element, in response to each of the interrogation pulses, to become cumulatively increased in intensity, for reliable detection by detection means, as a peak signal distinguishable from background noise, for detection of the tag and object attached thereto.

13. An apparatus for electronic detection of an object within a defined area, said apparatus comprising:

a transmitter that emits a pulsed wideband interrogation signal;

a low Q tag element affixed to an object, said tag element including a tag circuit that responds to each pulse of said pulsed wideband interrogation signal with a small narrowband return signal having a specific, but not predetermined frequency, said tag element being minimally sized and being so affixed relative to said object as to not interfere with the intended use of the object in a defined area;

a wideband receiver circuit that receives said small narrowband return signals, said receiver circuit comprising means for optimal reception within a predetermined distance from said tag element; and a signal processor, coupled to said wideband receiver circuit, that transforms said small narrowband return signals into a resulting narrowband return signal having sufficient strength to be distinguishable from ambient noise.

14. The apparatus of claim 13, wherein said tag circuit includes a ferrite rod, a coil wound around said ferrite rod, and a capacitive element coupled to said coil.

15. The apparatus of claim 13, wherein said tag circuit is encased in a protective casing configured in the shape of a bead, and wherein said bead has an overall length of between 5 to 12 millimeters.

16. The apparatus of claim 13, wherein said predetermined distance within which said wideband receiver circuit is adapted for optimal reception is between 12 to 18 inches from said tag element.

17. The apparatus of claim 13, wherein said signal processor comprises a boxcar integrator.

18. A method for the electronic detection of a foreign object used in a surgical site, said method comprising the steps of:

providing a minimally sized, passive device configured to emit a small narrowband response signal, characterized by a specific, but not predetermined response frequency, in response to an excitation signal including a specific, but not predetermined excitation frequency;

attaching said passive device to said foreign object so as to not interfere with the intended use of said foreign object in the surgical site;

using said foreign object in the surgical site;

scanning the surgical site with a plurality of pulses of a wideband interrogation signal that includes said specific, but not predetermined excitation frequency, said plurality of pulses being of sufficient duration and interval so as to cause said passive device to emit a plurality small narrowband response signals of increasing intensity;

utilizing a wideband receiver to receive said plurality small narrowband response signals; and transforming said plurality of small narrowband response signals into a resulting response signal of sufficient strength to be distinguished from ambient noise.

* * * * *